United States Patent
Ansmann et al.

(12) 
(10) Patent No.: US 6,229,056 B1
(45) Date of Patent: May 8, 2001

(54) UNSATURATED FATTY COMPOUNDS WITH IMPROVED LOW-TEMPERATURE BEHAVIOR

(75) Inventors: Achim Ansmann, Erkrath; Guenther Demmering, Solingen; Georg Assmann, Juechen; Fritz Schuster, Duesseldorf; Alfred Westfechtel, Hilden; Michael Koehler, Mettmann, all of (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 08/765,431

(22) PCT Filed: Jun. 22, 1995

(86) PCT No.: PCT/EP95/02440

§ 371 Date: May 8, 1997

§ 102(e) Date: May 8, 1997

(87) PCT Pub. No.: WO96/00768

PCT Pub. Date: Jan. 11, 1996

(30) Foreign Application Priority Data

Jun. 30, 1994 (DE) ................................................ 44 22 858

(51) Int. Cl.[7] .................................................. C07C 27/04
(52) U.S. Cl. ......................... 568/884; 568/876; 554/141; 554/142; 554/167
(58) Field of Search .................................. 568/876, 884; 554/167, 141, 142

(56) References Cited

U.S. PATENT DOCUMENTS

| 4,743,402 | * | 5/1988 | Fick ................................... 260/412.2 |
| 5,275,264 | * | 1/1994 | Heaton et al. ....................... 800/200 |
| 5,276,204 | * | 1/1994 | Schmid et al. ....................... 568/616 |
| 5,276,264 | | 1/1994 | Heaton et al. ....................... 800/200 |
| 5,514,820 | | 5/1996 | Assmann et al. .................... 554/167 |

FOREIGN PATENT DOCUMENTS

| 39 32 514 | 4/1991 | (DE) . |
| 370 273 | 5/1990 | (EP) . |
| 496 504 | 7/1992 | (EP) . |

OTHER PUBLICATIONS

Seifen–Öle–Fette–Wachese 109, 1983, p. 225.
Ullmann's Enzyklopaedie der technischen Chemie, Verlag Chemie, Weinheim, 4th Ed., vol. 11. pp. 436 et seq., 1988.
Seifen–Öle–Fette–Wachse 114, 1988, p. 595.

\* cited by examiner

*Primary Examiner*—Deborah D. Carr
(74) *Attorney, Agent, or Firm*—John E. Drach; Martin G. Meder; Real J. Grandmaison

(57) ABSTRACT

The proposal is for unsaturated fatty substances with improved cold behavior obtained by (a) transesterifying a new low stearic (LS) sunflower oil with an oleic acid content of over 85 wt. % and a stearic acid content of under 3 wt. %, and (b) hydrogenating the resultant methyl esters in the prior art manner into the corresponding unsaturated fatty alcohols in the iodine number range from 90 to 100. The fatty substances are also distinguished by improved color and odor and are suitable for making fatty chemical products, e.g. alkoxylates, ether sulphates, sulphates and esters.

18 Claims, No Drawings

UNSATURATED FATTY COMPOUNDS WITH IMPROVED LOW-TEMPERATURE BEHAVIOR

This application is a 371 of PCT/EP95/02440 filed Jun. 22, 1995.

FIELD OF THE INVENTION

This invention relates to unsaturated fatty compounds with improved low-temperature behavior which are obtained by transesterifying new LS sunflower oil with methanol and hydrogenating the resulting methyl esters with the double bonds intact to form the corresponding fatty alcohols. The invention also extends to derivatives of the unsaturated fatty alcohols, to processes for their production and to their use for the production of surface-active formulations. Finally, the invention relates to the use of the new LS sunflower oil for the production of unsaturated fatty alcohols.

BACKGROUND OF THE INVENTION

Fatty compounds, more particularly unsaturated fatty alcohols, are important intermediate products for a large number of products of the chemical industry, for example for the production of surfactants and cosmetic products. An overview of this subject was published, for example, by U. Ploog et al. in Seifen-Öle-Fette-Wachse 109, 225 (1983).

Unsaturated fatty alcohols cannot be produced on the basis of petrochemical raw materials and processes. Instead, they are produced from more or less unsaturated fatty acids or methyl esters thereof based on renewable raw materials which are hydrogenated with the double bonds intact, for example in the presence of chromium- and/or zinc-containing mixed oxide catalysts [cf. Ullmann's Enzyklopaedie der technischen Chemie, Verlag Chemie, Weinheim, 4th Edition, Vol. 11, pages 436 et seq.].

Basically, unsaturated fatty alcohols can be produced in three ways:

1. Fats and oils are subjected to pressure hydrolysis with water. After removal of the water-containing glycerol, split fatty acids representing mixtures of saturated and unsaturated fatty acids are obtained. Since the co-hydrogenation of these acids is unable to influence the ratio of saturated and unsaturated components, it is only possible in this way to obtain fatty alcohols with a low iodine value below 80 and preferably in the range from 50 to 55.
2. The separation of saturated and unsaturated fatty acids by distillation is only possible with a disproportionately high outlay on equipment. In contrast to (1), however, the split fatty acids can be converted by "roll-up separation" into a predominantly saturated fatty acid cut and a predominantly unsaturated fatty acid cut. Hydrogenation of the unsaturated fatty acid cut gives technical oleyl alcohols with iodine values of around 80 to 85 which, on an industrial scale, are further processed by fractional distillation or winterizing to form products with iodine values of 90 to 100.
3. It is also possible to subject highly unsaturated vegetable oils to transesterification in which the methyl esters accumulate with a relatively small percentage of saturated homologs. Roll-up separation is neither possible nor necessary in this case because the hydrogenation directly provides highly unsaturated fatty alcohols (iodine value >100).

The three processes mentioned have long been commercially used for the production of unsaturated fatty alcohols which, unfortunately, are attended by a number of disadvantages:

The products obtainable by method 1 have an iodine value below 80 and are wax-like. Apart from the unfavorable solidification point, they do of course have only some of the advantages associated with the unsaturated structure.

Fats and oils with iodine values of 40 to 70, for example beef tallow, lard, palm oil or palm stearin, are normally used as raw materials for method 2. The resulting fatty alcohols have an iodine value of 90 to 100 and, by virtue of their property profile, are the most suitable for use on an industrial scale. However, they are often unsatisfactory both in regard to their color and in regard to their odor quality and have an unfavorably high solidification or cloud point for many applications. The same also applies to unsaturated fatty alcohols with iodine values in the same range based on conventional new sunflower oil which, on account of its high content of oleic acid, could also be used as a starting material despite its low content of polyunsaturated fatty acids.

Rapeseed oil, olive oil, linseed oil or peanut oil, for example, are suitable for the production of highly unsaturated fatty alcohols by method 3. However, highly unsaturated fatty alcohols, for example those based on new rapeseed oil low in erucic acid, contain a significant percentage of polyunsaturated homologs and, accordingly, are susceptible to autoxidation processes.

Accordingly, the problem addressed by the present invention was to provide unsaturated fatty alcohols with an iodine value of 90 to 100 based on vegetable raw materials—and corresponding derivatives—which would be distinguished in particular by improved low-temperature behavior.

DESCRIPTION OF THE INVENTION

The present invention relates to unsaturated fatty compounds with improved low-temperature behavior obtainable by (a) transesterifying new LS sunflower oil with an oleic acid content of more than 85% by weight and a stearic acid content of less than 3% by weight with methanol and (b) hydrogenating the resulting methyl esters in known manner to form the corresponding unsaturated fatty alcohols with iodine values of 90 to 100.

It has surprisingly been found that vegetable fatty alcohols with iodine values of 90 to 100 which not only show extremely good color and odor properties, but are also distinguished as required by particularly favorable low-temperature behavior, can be obtained by the use of new sunflower oil with a low content of stearic acid (LS="low stearic"). A particular feature of the unsaturated fatty alcohols according to the invention compared with technical oleyl alcohol based on "conventional" new sunflower oil (i.e. a sunflower oil with an oleic acid content of about 80 to 85% by weight and a stearic acid content of less than 3% by weight) is that they have a surprisingly low cloud point (1° C. as opposed to 18° C.).

Other advantageous embodiments of the invention are derivatives which also show favorable low-temperature behavior coupled with improved odor and color properties and which are obtained in known manner by subjecting the unsaturated fatty alcohols mentioned at the beginning to alkoxylation;

alkoxylation, sulfation and neutralization;

sulfation and neutralization; or esterification with aliphatic carboxylic acids containing 1 to 22 carbon atoms and 0 and/or 1 to 3 double bonds.

Production process

The present invention also relates to a process for the production of unsaturated fatty compounds with improved low-temperature behavior, in which (a) new LS sunflower oil with an oleic acid content of more than 85% by weight and a stearic acid content of less than 3% by weight is transesterified with methanol and
(b) the resulting methyl esters are hydrogenated in known manner to form the corresponding unsaturated fatty alcohols with iodine values of 90 to 100.

New LS sunflower oil

The new low-stearic (LS) sunflower oil is, for example, a commercially available vegetable oil which is marketed by the Pioneer Corporation, USA [cf. EP-A1 0 496 504, U.S. Pat. No. 5,276,264] and which has the typical composition shown in Table 1 below:

TABLE 1

Composition of New LS Sunflower Oil

| Fatty Acid Components | Content % By Weight |
|---|---|
| Palmitic acid | 2 to 5 |
| Stearic acid | 0.5 to 2 |
| Oleic acid | 85 to 95 |
| Linoleic acid | 3 to 5 |

A particular characteristic of this new vegetable oil is that it contains more than 85% by weight and preferably more than 90% by weight of oleic acid and less than 3% by weight of stearic acid.

Transesterification

By transesterification (alcoholysis) is meant the replacement of one alcohol bound in the ester by another. The transesterification of triglycerides with methanol proceeds in accordance with reaction equation 1:

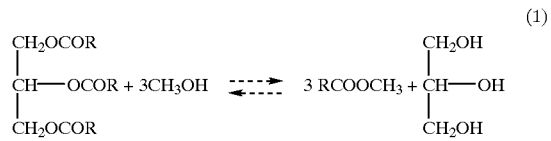

(1)

Transesterification like esterification is an equilibrium reaction. Accordingly, an excess of methanol or removal of the glycerol is recommended in order to displace the equilibrium of the reaction onto the methyl ester side.

The replacement of the glycerol component of fats by monohydric alcohols, such as methanol, can be carried out without difficulty even at low temperatures. Pre-deacidified oils and fats are preferably used for processing. They are mixed with an excess of pure methanol in the presence of an alkaline catalyst (for example a zinc soap) at temperatures of around 50 to 70° C. After a corresponding residence time, the glycerol collects substantially free from water at the bottom of the reaction vessel. The transesterification reaction is terminated when no more glycerol is present in the methyl ester formed. In this batch procedure, the reaction equilibrium can of course be considerably increased by higher temperatures.

However, the transesterification reaction is preferably carried out continuously either in the absence of pressure at around 70° C. or under excess pressure (10 to 90 bar, 200 to 260° C.).

The triglycerides are normally delivered to the transesterification reactor in co-current with the methanol, which is used in several times the molar quantity, by means of metering pumps. At the same time, the necessary quantity of catalyst is introduced. By venting the reactor, the transesterification mixture (methyl ester, glycerol, methanol) enters a methanol and glycerol separation unit consisting essentially of a plate column and a glycerol separator. The water-containing methanol removed is concentrated in the enriching section of the column. The pure methanol is condensed and returned to the transesterification process. In the separator, the remaining solution separates into a methyl ester phase, which is purified in a following distillation stage, and a glycerol phase (glycerol content >90% by weight) which is also worked up. Pressureless or low-pressure transesterification processes are described, for example, in an article by Davidsohn in Seifen-Öle-Fette-Wachse 114, 595 (1988) and in DE-A1 39 32 514 (Henkel).

Hydrogenation

The reduction of esters with metallic sodium in the presence of an alcohol was discovered by Bouveault and Blanc in 1903. Nowadays, however, the production of fatty alcohols on an industrial scale is carried out almost exclusively by high-pressure hydrogenation of distilled or fractionated methyl ester or fatty acid cuts in one or more fixed-bed or shaft reactors arranged in tandem at temperatures of 200 to 250° C. and under a hydrogen pressure of 200 to 300 bar. To this end, the fatty acid or methyl ester is continuously forced into the installation against the hydrogen pressure, heated to the reaction temperature and introduced at the head of the reactor. Adkins catalyst beds based on Cu/Cr/Zn and/or Cu/Cr/Cd mixed oxides are normally used for the production of unsaturated fatty alcohols. In this case, the carboxyl(ate) group is selectively hydrogenated with the double bonds present in the fatty residue intact.

In addition to the fixed-bed procedure, the hydrogenation may also be carried out in the trickle phase. In this variant, too, fatty acid or ester and hydrogen flow through the reactor from above at a temperature of 200 to 300° C. and under a pressure of 250 to 300 bar. In this case, however, the quantities of recycle gas and the molar excess of hydrogen are considerably smaller which is reflected in smaller plant dimensions. Silica gel supported catalysts containing 20 to 40% by weight of the copper chromites mentioned at the beginning are used as catalysts. Although these catalysts have high mechanical stability, they are more susceptible to poisoning than solid catalysts on account of their low content of active substance and, accordingly, have short lives.

The resulting fatty alcohols are then preferably purified by distillation in known manner with removal of first runnings (around 5% by weight).

Derivatization

As mentioned at the beginning, the present invention also includes the observation that the excellent properties of the unsaturated fatty alcohols initially produced remain intact even after derivatization. This includes:

Alkoxylation. Alkoxylates of the unsaturated fatty alcohols are obtained in known manner by addition of ethylene and/or propylene oxide in the presence of basic catalysts, for example sodium methylate or calcined hydrotalcite, and may have both a conventional homolog distribution and a narrow homolog distribution. The alkoxylates are suitable, for example, as raw materials for detergents, as emulsifiers in the textiles field, in drilling and cutting oils and in cosmetic formulations.

Alkoxylation/sulfation. Ether sulfates of the unsaturated fatty alcohols are obtained in known manner by alkoxylation, subsequent sulfation with gaseous sulfur trioxide or chlorosulfonic acid and, finally, neutralization with bases. The products are suitable as raw materials for detergents.

Sulfation. Fatty alcohol sulfates based on the unsaturated alcohols are obtained in known manner by sulfation with gaseous sulfur trioxide or chlorosulfonic acid and subsequent neutralization with bases. The products are also suitable as detergents for raw materials and as textile auxiliaries.

Esterification. Esters of the unsaturated fatty alcohols are obtained in known manner by catalytic reaction with aliphatic carboxylic acids containing 1 to 22, preferably 6 to 22 and more preferably 12 to 18 carbon atoms and 0 and/or 1 to 3 double bonds. Typical examples are reactions of a technical oleyl alcohol according to the invention (iodine value 95) with acetic acid, $C_{6-10}$ head-fractionated fatty acid, lauric acid, palmitic acid, stearic acid, oleic acid, $C_{12/14}$ cocofatty acid, $C_{12/18}$ cocofatty acid or $C_{16/18}$ tallow fatty acid. The products are suitable, for example, as oils for the production of cosmetic formulations.

Commercial Applications

The unsaturated fatty compounds according to the invention are distinguished from known products by an improved odor, an improved color and, in particular, by more favorable low-temperature behavior.

The present invention also relates to their use—either on their own or in the form of mixtures with known unsaturated fatty compounds—for the production of surface-active formulations, for example superfatting agents or solvents for active substances, creams, emollients and lotions, lubricants for the machining of metals and antifoam agents in dispersion paints, in which they may be present in quantities of 1 to 75% by weight and preferably 5 to 50% by weight, based on the particular product.

Finally, the present invention relates to the use of new LS sunflower oil containing more than 90% by weight of oleic acid and less than 3% by weight of stearic acid for the production of unsaturated fatty alcohols with iodine values of 90 to 100 by transesterification and hydrogenation.

EXAMPLES

General Production Procedures

Example 1

The starting materials were transesterified with methanol and freed from glycerol and unreacted methanol. The resulting methyl ester mixture was hydrogenated after distillation with the double bonds intact. The product was then purified by distillation.

Example 2

The starting materials were subjected to pressure hydrolysis and the glycerol/water mixture was removed. The resulting split fatty acid mixture was separated by roll-up separation into a stearin fraction and an olein fraction. The olein which contained around 70% by weight of oleic acid was then hydrogenated with the double bonds intact. The product was then purified by distillation.

The composition of the raw materials used is shown in Table 2 (percentages as % by weight). Table 3 shows the performance data of the resulting unsaturated fatty alcohols.

TABLE 2

Raw Materials Used

| Fatty Acid Component | LS % | NS % | BT % |
| --- | --- | --- | --- |
| Palmitic acid | 4 | 5 | 5 |
| Stearic acid | 1 | 4 | 2 |
| Oleic acid | 91 | 85 | 68 |
| Linoleic acid | 4 | 5 | 12 |

Legend:
LS = New low-stearic sunflower oil (Pioneer Corp., USA)
NS = New Sunflower oil (SFO Enterprises USA)
BT = Basis beef tallow; the composition of the technical oleic acid Edenor ® F-TiO₅ (Henkel KGaA, FRG) obtained after the roll-up separation is shown in the interests of a fairer comparison.

TABLE 3

Characteristic Data of the Products

Unsaturated Fatty Alcohol

| Example | Raw Material | IV | Method | CP ° C. | Color APHA | Odor |
| --- | --- | --- | --- | --- | --- | --- |
| 1 | LS-NSF oil | 93 | 1 | 1.0 | 10 | ++ |
| C1 | NSF oil | 88 | 1 | 18.0 | 15 | + |
| C2 | Beef tallow | 95 | 2 | 8.0 | 100 | − |

Legend:
IV = Iodine value
CP = Cloud Point
Odor = ++]= odorless + = slight odor − = distinct odor

What is claimed is:

1. A process for the production of unsaturated fatty compounds, comprising the steps of:
    transesterifying sunflower oil having an oleic acid content of more than about 85% by weight and a stearic acid content of less than about 3% by weight with methanol to form methyl esters thereof; and
    hydrogenating the resulting methyl esters to form the corresponding unsaturated fatty alcohols, whereby said unsaturated fatty alcohols have iodine values of about 90 to about 100.

2. Unsaturated fatty alcohols produced by the process of claim 1.

3. A process as claimed in claim 1, further comprising the step of alkoxylating said unsaturated fatty alcohols to form unsaturated fatty alcohol alkoxylates.

4. Unsaturated fatty alcohol alkoxylates produced by the process of claim 3.

5. A process as claimed in claim 1, further comprising the steps of:
    sulfating said unsaturated fatty alcohols to form unsaturated fatty alcohol sulfates; and
    neutralizing said unsaturated fatty alcohol sulfates to form unsaturated fatty alcohol sulfate salts.

6. Unsaturated fatty alcohol sulfate salts produced by the process of claim 5.

7. A process as claimed in claim 1, further comprising the steps of:
    alkoxylating said unsaturated fatty alcohols to form unsaturated fatty alcohol alkoxylates,
    sulfating said unsaturated fatty alcohol alkoxylates to form unsaturated fatty alcohol alkoxylate sulfates; and
    neutralizing said unsaturated fatty alcohol alkoxylate sulfates to form unsaturated fatty alcohol alkoxylate sulfate salts.

8. Unsaturated fatty alcohol alkoxylate sulfate salts produced by the process of claim 7.

9. The process as claimed in claim 1 further comprising the step of esterifying said unsaturated fatty alcohols with aliphatic carboxylic acids containing about 1 to about 22 carbon atoms to form unsaturated fatty esters.

10. The process as claimed in claim 9, wherein said aliphatic carboxylic acids contain 1 to 3 double bonds.

11. Unsaturated fatty esters produced by the process of claim 9.

12. Surface-active formulations containing the unsaturated fatty compounds claimed in claim 1.

13. Surface-active formulations as in claim 12 further containing known unsaturated fatty compounds.

14. In a process for the production of unsaturated fatty alcohols having iodine values of about 90 to about 100 by transesterification and hydrogenation, wherein the improvement comprises transesterifying and hydrogenating a sunflower oil having an oleic acid content of more than about 85% by weight and a stearic acid content of less than about 3% by weight.

15. An unsaturated fatty alcohol composition, said composition having iodine values of about 90 to about 100 and a cloud point of less than about 8° C.

16. The unsaturated fatty alcohol composition of claim 15, said composition having a cloud point not greater than about 1° C.

17. In a process for producing formulations having surface-active properties, wherein the improvement comprises adding to said formulations the unsaturated fatty alcohol claimed in claim 15.

18. In a process for producing formulations as in claim 17, wherein the improvement further comprises mixing said formulations with known unsaturated fatty compounds.

* * * * *